United States Patent [19]
Skidmore

[11] Patent Number: 5,575,289
[45] Date of Patent: Nov. 19, 1996

[54] FLOWMETERS

[75] Inventor: Robert Skidmore, Bitton, England

[73] Assignee: British Technology Group Limited, London, England

[21] Appl. No.: 362,601

[22] PCT Filed: Jul. 16, 1993

[86] PCT No.: PCT/GB93/01498

§ 371 Date: Jan. 11, 1995

§ 102(e) Date: Jan. 11, 1995

[87] PCT Pub. No.: WO94/02069

PCT Pub. Date: Feb. 3, 1994

[30] Foreign Application Priority Data

Jul. 17, 1992 [GB] United Kingdom ............ 9215231

[51] Int. Cl.$^6$ ............................................. A61B 8/00
[52] U.S. Cl. .................................................. 128/661.08
[58] Field of Search ............... 128/660.08, 660.09, 128/660.1, 661.08, 661.09, 661.1, 662.04

[56] References Cited

U.S. PATENT DOCUMENTS

| | | | |
|---|---|---|---|
| 4,246,791 | 1/1981 | Glenn | 128/660.1 |
| 4,313,444 | 2/1982 | Glenn | 128/661.09 |
| 4,317,370 | 3/1982 | Glenn . | |
| 4,509,526 | 4/1985 | Barnes et al. . | |
| 4,546,771 | 10/1985 | Eggleton et al. . | |
| 4,757,823 | 7/1988 | Hofmeister et al. . | |
| 5,054,492 | 10/1991 | Scribner et al. | 128/660.09 |
| 5,085,220 | 2/1992 | Nudell et al. | 128/662.04 |

FOREIGN PATENT DOCUMENTS

| | | |
|---|---|---|
| 62390 | 10/1982 | European Pat. Off. . |
| 110593 | 6/1984 | European Pat. Off. . |
| 329492 | 8/1989 | European Pat. Off. . |
| 2099997 | 12/1982 | United Kingdom . |

Primary Examiner—George Manuel
Attorney, Agent, or Firm—Cushman, Darby & Cushman

[57] ABSTRACT

The invention provides a probe and method for measuring parameters of fluid flow in a conduit within a human or animal body, with specific application to non-invasive measurement of the cross-sectional area of blood vessels, particularly the ascending aorta (24). A probe (1) contains an ultrasound transducer (2) and an acoustic reflector (4) drivable in an oscillatory manner by an electric motor (8). A narrow ultrasound beam (15) is directed downwardly via the suprasternal notch and swept by the reflector through an arc. The probe has an external dimension transverse to the ultrasound beam path which reduces substantially from the region of the transducer to the region where the beam exits the probe. The invention has application in monitoring cardiac output.

12 Claims, 2 Drawing Sheets

FLOWMETERS

The present invention relates to the measurement of parameters of fluid flow in a conduit within a human or animal body. It has more specific application to flowmeters of Doppler ultrasound form, and in a particular application is for use in monitoring a patient's blood flow.

Flowmeters of the Doppler ultrasound type are routinely used in medical practice for measuring and monitoring blood flow in patients. These meters are usually designed for transcutaneous application, but some have been developed for catheterised application into a blood vessel of interest. A device suitable for invasive ultrasonic investigation is described in U.S. Pat. No. 4,546,771. This device comprises a needle with a sharp point for insertion into a human body, the needle containing transducer means and beam directing means for directing acoustical beams radially from the needle to a point outside of the needle.

Meters known from the prior art are often limited to the provision of measures only of blood velocity, whereas the medical community frequently has an interest in knowing the blood volume flow rate in the relevant vessel. This interest extends particularly to the case in which the vessel is the ascending aorta because the rate is then an effectively direct indication of cardiac output. Blood velocity may be measured using the Doppler ultrasound method, and blood volume flow rate is provided simply as the product of velocity and the vessel cross-sectional area. The velocity used in such a calculation is a weighted average velocity value to take into account the velocity distribution across the vessel diameter. A problem remains in attaining an indication of the area in question, and in the case of the interest in cardiac output, area is often estimated for a given patient by way of a quite separate imaging procedure. Margins of error for such measurements can be as high as 20%. Access for non-invasive ultrasound monitoring equipment to the aorta presents particular problems, as the sternum of the body provides an effective screen to ultrasound signals. Access is possible via the suprasternal notch, but this space is very limited in size.

It is an object of the present invention to improve this situation and to this end there is provided, according to one aspect of the invention, a medical probe suitable for use in measuring parameters of fluid flow in a conduit within a human or animal body, the probe comprising:

a hollow housing having an ultrasound transparent wall part;

transducer means mounted within the housing and operable to emit and detect ultrasound beam signals along a path; and reflecting means within the housing and disposed in said path to divert the beam through an angle so as to emerge from the housing through an exit portion of the ultrasound transparent wall part;

wherein the external dimension of the housing transverse to said path reduces substantially from the region of the transducer means to the region of the exit portion, characterised in that the reflecting means are mounted for rotation in the narrowed exit portion region.

Preferably, the probe has a distal part with a smoothly contoured external shaping to permit safe non-invasive use.

The type of transducer used in a scanning ultrasound device is likely to be of relatively large size, as a narrow ultrasound beam is required, necessitating a relatively large crystal. However the very restricted access provided by the suprasternal notch renders it very difficult to introduce a probe with a large transducer directly into the notch. The particular advantage of the invention is that the part of the probe where the exit section is situated can be located within the notch, and by use of a rotatable reflecting means the ultrasound beam can be scanned whilst the transducer means itself remains at some distance from the access point.

Mounting the reflecting means in the region of the exit portion allows the use of a small rotating reflector in the tip of the probe.

Preferably, the drive means to rotate the reflecting means is mounted within the housing. The drive means may be adapted to rotate the reflecting means in an oscillatory fashion, or alternatively, in a continuous unidirectional fashion.

In a preferred form, the reflecting means is mounted for rotation about an axis lying along said beam path.

Preferably, the transducer means and the reflecting means are linked to rotate together. In this way, the relative orientation between the transducer means and the reflecting means remains unchanged during operation. This has the advantage that small inaccuracies in alignment of the parts, or the distribution of beam intensity across the beam section, will automatically be compensated for and not lead to variation in the characteristics of the ultrasound beam across the range of its sweep.

Preferably, the reflecting means is mounted at an angle of about 45° to the direction of said beam path. When the reflecting means is rotated about an axis lying along the beam path, this means that the beam will sweep out a planar arc.

The invention also embraces apparatus for measuring parameters of fluid flow in a conduit within a human or animal body, comprising a probe according to the above definition and signal processing means to analyse Doppler components of the returning ultrasound signals.

According to another aspect of the invention, there is provided a method for measuring parameters of fluid flow in a conduit within a human or animal body using the probe defined above, which method comprises:

locating the probe to position the exit portion adjacent the skin of the body;

operating the transducer means to emit an ultrasound beam;

directing the ultrasound beam by way of the reflecting means substantially along the conduit;

rotating the reflecting means so as to sweep the ultrasound beam through an arc;

detecting ultrasound beam signals returning from at least one range of the beam sweep and analysing the returning signals.

The parameters which can be determined by way of this invention include the vessel diameter, from which an estimation of the cross-sectional area of fluid flow, and hence of the vessel, can be made, and the velocity values at a successive set of points across the appropriate diameter or section, which can be determined by the value of the Doppler signals from the set of points. From these parameters fluid volume flow can be estimated. If data is taken from a number of different ranges, from the beam origin then it is possible to monitor the behaviour of the fluid within the conduit over a longitudinal portion of the conduit.

In a specific application of the method of invention, the conduit is the ascending aorta and the beam is directed by way of the suprasternal notch. Blood flow monitoring thereby gives an indication of cardiac performance.

The invention will be further described by way of example with reference to the accompanying drawings, in which.

Figure 3:
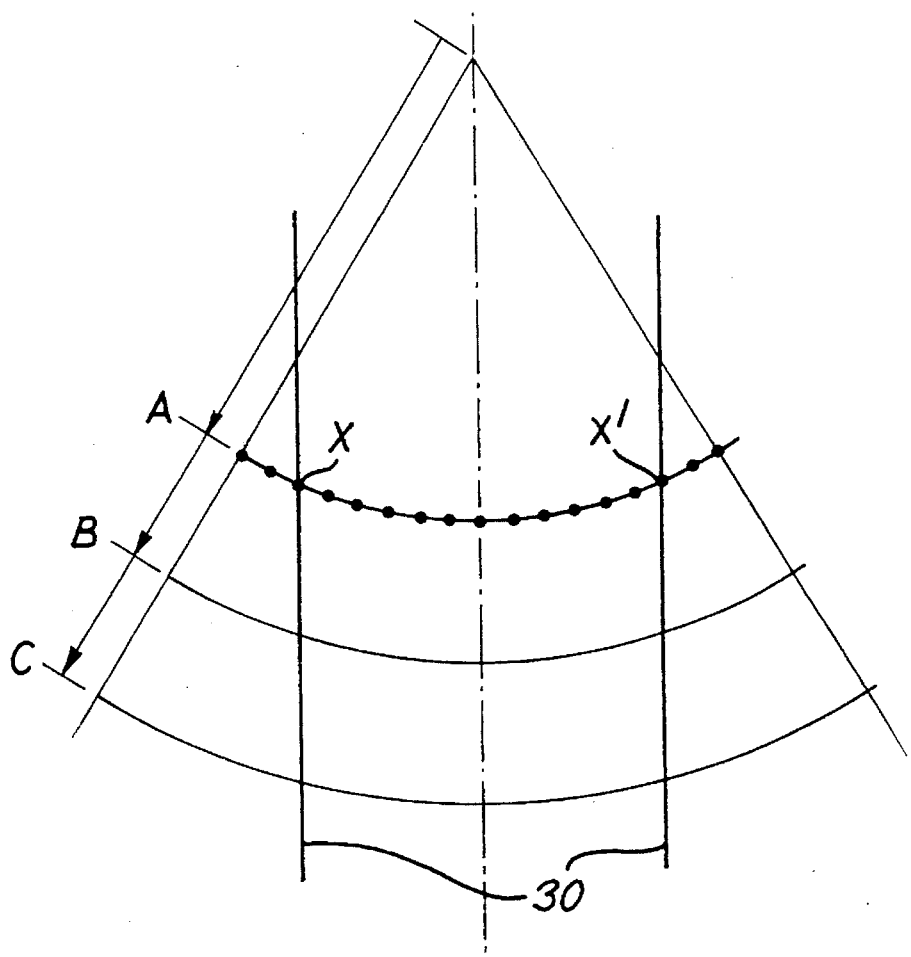
Figure 4:
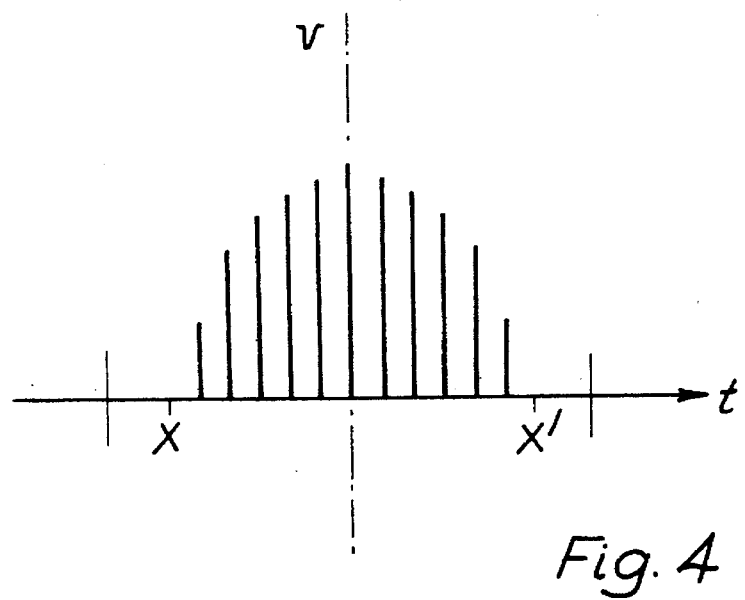

FIGS. 3 and 4 graphically illustrate details of the implementation of the invention.

Figure 1:
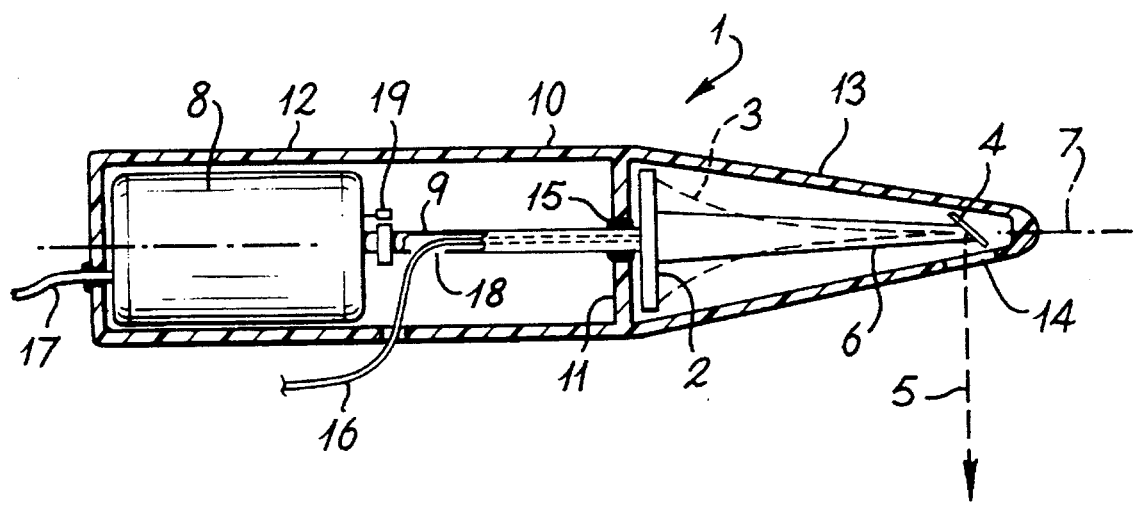
FIG. 1 illustrates one embodiment of the apparatus for carrying out the invention.

A preferred form of the apparatus for producing and directing the ultrasound beam according to the invention is illustrated in FIG. 1. The apparatus comprises an ultrasound probe 1 which includes a transducer 2 consisting of a piezoelectric crystal of planar disc form designed to produce a narrow ultrasound beam. The beam is represented by dotted lines and denoted by reference 3. The electrical signal driving the transducer is carried by a cable 16. The probe 1 also includes an acoustic reflector 4, for example a planar disc of stainless steel, arranged to intercept and divert the beam 3. The reflector 4 is set at an angle of 45° to the direction of propagation of the beam in order to divert the beam through a right angle, but other reflector angles are of course possible, the angle being selected as appropriate. The resulting diverted narrow beam is designated in FIG. 1 by the dotted line of reference 5.

The transducer and the reflector are rigidly connected to one another by means of two or more arms spaced apart from one another, one of which is shown in FIG. 1 as reference 6. These arms extend between the circumference of the transducer 2 and that of the reflector 4 and ensure that relative movement between transducer and mirror is not permitted. The transducer is rigidly attached to one end of a hollow drive shaft 9 of a motor 8 such that drive shaft 9, transducer 2 and reflector 4 can be rotated by the motor about axis 7, which is the centre line of the propagated ultrasound beam 3. Motor 8 is preferably a d.c. stepping motor capable of oscillating through a fixed known angle at a known speed of rotation. Such oscillatory rotation will therefore produce a narrow ultrasound beam 5 which executes a cyclic plane polar sweep perpendicular to the axis 7. An encoder, such as an optical encoder 19, is provided on drive shaft 9.

The motor, the transducer and the reflector are all mounted within a probe housing 10 which is made up of two parts, a cylindrical proximal part 12 and a tapered distal part 13. The proximal part 12 encloses the motor 8 whilst the tapered distal part 13 contains the transducer and reflector combination. An ultrasound window 14 is provided in the side wall of the tapered distal part 13 adjacent to the reflector 4 to enable transmission of the ultrasound beam. The window consists of a clear plastics material with very low acoustic attenuation. The probe 1 is designed to be easily manipulable by an operator who holds the cylindrical proximal part 12, whilst the tip of the tapered distal part 13, in which the reflector 4 is located, is shaped and sized to fit within the limited space provided by the patient's suprasternal notch. As an example, a probe measuring 12 cm in length may be used whose diameter narrows from 2.5 cm in the region of the transducer to considerably less in the region of the tip.

The probe housing further comprises an internal partition 11 which separates the spaces enclosed by the two parts 12 and 13, a bore in the centre of this partition enabling the hollow motor drive shaft 9 to pass through. A fluid seal 15 is provided between the drive shaft and the partition 11. The cable 16 passes from the outside of the probe into the interior of the proximal part 12 of the probe housing and then into the hollow drive shaft 9 through an opening 18 in the wall of the latter. The cable 16 is connected to transducer 2. A second cable 17 supplies power to the motor 8.

The space enclosed by the tapered part 13 of the probe housing is filled with a mineral oil which is prevented from passing into the part 12 of the housing containing the motor and cables by the seal 15. The mineral oil is selected both for its acoustic properties and to avoid cavitation.

The transducer 2 acts as an ultrasound transmitter/receiver, although it is envisaged that separate transmission and reception elements could be employed.

Figure 2:
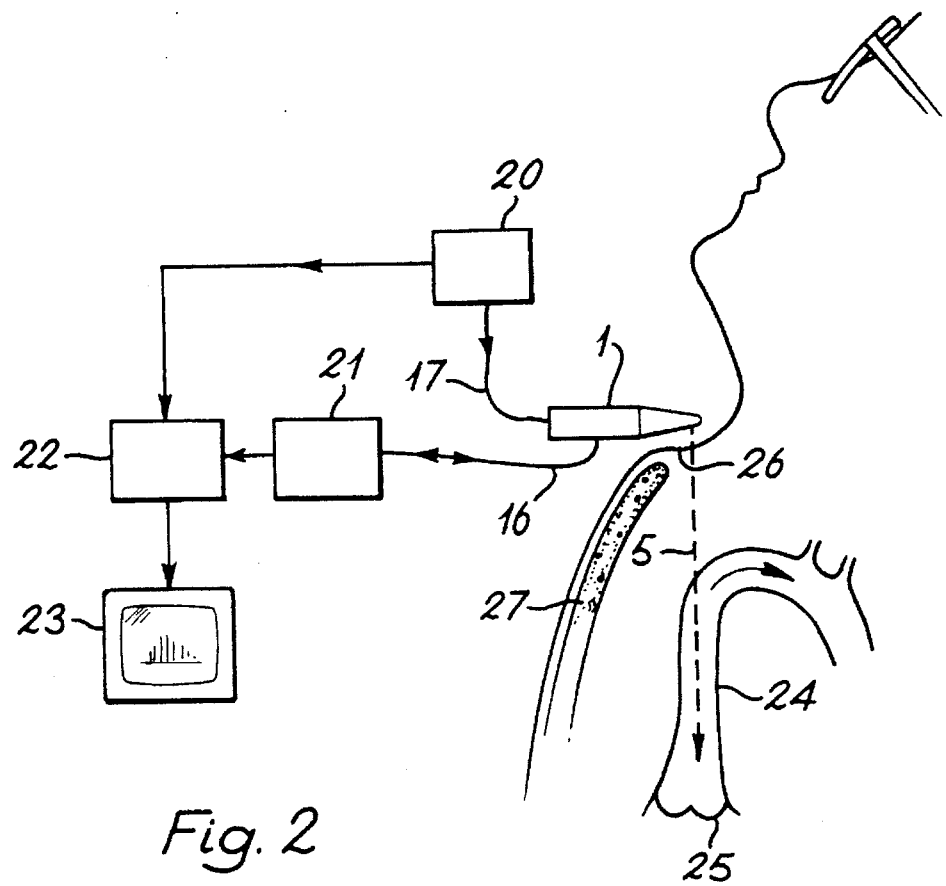
FIG. 2 illustrates schematically the implementation of the invention.

The implementation of the invention is schematically shown in FIG. 2. A transmitter/receiver system 21 and a Doppler signal processing apparatus 22 of digital multigated Doppler type are utilised. The transmitter includes an ultrasound frequency oscillator supplying power to the transducer 2 via cable 16 in a pulsed wave mode to produce the ultrasound beam. Between transmission pulses the transducer detects ultrasound signals and by opening a single gate in the receiving circuit signals can be admitted returning from a discrete range within the medium being investigated, that range being known from the time delay between transmission and detection of the ultrasound beam. By opening successive gates in the receiving circuit signals are admitted from a series of successive ranges, and thus specific data is received about the individual depths at which the signals are gathers. Much work has been carried out in developing instrumentation for applying Doppler ultrasound techniques to investigating movement of blood in its vessels and it is not intended to describe this specifically here, but details about such instrumentation and associated processing are described in 'Doppler Ultrasound—Physics, Instrumentation and Clinical Applications' by D. H. Evans, W. N. McDicken, R. Skidmore and J. P. Woodcock, published by John Wiley & Sons, 1989.

The apparatus also includes a power source and sweep control 20 for the motor. Power is supplied to the motor via cable 17 to drive the motor in the appropriate oscillatory manner. By virtue of the encoder 19, at a given point in time the angular position of the beam can be determined.

FIG. 2 also depicts the ultrasound probe 1 being used to investigate the ascending aorta 24 downstream of the aortic valve 25. The beam 5, which as already explained emerges laterally from the probe 1 due to the reflector 4, is directed downwardly by way of the suprasternal notch 26 along the ascending aorta 24. The suprasternal notch provides a small 'window' through the patient's sternum 27. When correctly directed therethrough, the beam sweeps out an arc of a specific angle across the width of the aorta, that angle depending on the angle of oscillation of the transducer/reflector combination provided by the motor 8.

FIGS. 3 and 4 provide a diagrammatic illustration of the principle of the method according to the invention. The electronics of the Doppler signal processing device 22 permit information to be gathered from Doppler signals emanating from specific ranges in the beam sweep and at specific known angles across the sweep, known from the sweep control of device 20. The information can be presented on a monitor 23 or otherwise in an appropriate manner for real-time monitoring of the operation of the device. The wall of the aorta is designated by reference 30 and three different ranges at successively increasing distances from the beam source are designated respectively by reference letters A, B and C. As the beam makes a sweep across the vessel the Doppler signal processing means 22 detects the Doppler components of the received signal due to the movement towards the transmitter/receiver transducer 1 of the corpuscles in the moving blood at, say, range A. If, during its sweep, the beam extends beyond the vessel wall at this range, as is the case at range A, then the signals will be zero at the outer edges of the beam sweep. A Doppler signal will only be received from the points where moving blood is detected, in other words between points X and X'. The angles and range of these points are known, and so the positions of the points can be determined. Once processed, the signals at different points in the beam sweep can therefore give an image of the fluid in the vessel at that range as schematically illustrated in FIG. 4. The image will have a markedly distinctive segment for that portion of the beam sweep between the angular directions at which the beam is incident on the vessel wall at that range, and from this the diameter of the vessel can be determined, or at least the diameter of the flow within the vessel which is the more useful piece of information. Assuming the aorta to be circular in section, a cross-sectional area can therefore be determined.

Furthermore, velocity values can be determined from the Doppler signals from specific points across the beam sweep to give an indication of the velocity distribution profile across the blood vessel, and by multiplying the weighted average velocity by the measured cross-sectional area the blood flow can be estimated. The technique of Doppler colour flow mapping can be used to obtain a useful visual representation of the velocity profile.

In use, the operator orientates the probe 1 whilst monitoring the image on the screen. For example, the operator can move the probe in the direction perpendicular to the direction of sweep to determine when the beam is producing the widest Doppler image and therefore ensure that it is sweeping across the full diameter of the vessel. The monitoring range is selected as appropriate for the patient, for example, a range of 6 cm from the probe tip for an adult or 2.5 cm in the case of a neonate, and can then be altered if required in specific circumstances.

In monitoring the performance of the heart it is often required to determine the maximum blood flow in the aorta in order to give a measure of cardiac output at peak systole. This is achieved with the method of the present invention by triggering the apparatus to admit data from a beam sweep when the maximum velocity at a certain point has been detected by the Doppler signal processing means. The aortic diameter varies over the cardiac cycle so is also likely to be at a maximum at this point in time. A flow measurement thus obtained gives a representation of peak systolic cardiac output. If at the same point in time Doppler signals are detected from other ranges, for example ranges B and C in FIG. 3, then an instantaneous image of the moving fluid over a longitudinal section (a 'range cell') of the conduit can be obtained, for example over the full length of a passing pulse.

Pulse frequency, beam sweep speed, and other variables can clearly be selected as appropriate, but as an example pulsed ultrasound at 8 kHz can be used and the beam can be swept at a frequency of 10 cycles/s.

The embodiments of the invention illustrated in the figures and described above are given by way of example only and it will be understood that these in no way limit the scope of the invention which is taken to include all embodiments that fall within the spirit and scope of the appended claims. For example, as an alternative to the motor driving the transducer/reflector combination in an oscillatory manner the beam may be driven in continuous rotation, the ultrasound signals only being transmitted and/or received over the angular portion embracing the region under investigation.

The reflector 4 may furthermore itself be adjustable to alter the incident angle in order to alter the position of the emergent beam according to specific circumstances.

The data provided by the signal processing system, besides being displayed on monitor 23 in image form, can be stored in a computer memory or on disc for later retrieval. Similarly, a printer can be added to the system in order to produce hard copies of the data in image form or otherwise.

I claim:

1. A medical probe (1) suitable for use in measuring parameters of fluid flow in a conduit within a human or animal body, the probe comprising:

a hollow housing (10) having an ultrasound transparent wall part (14);

transducer means (2) mounted within the housing and operable to emit and detect ultrasound beam signals along a path (3); and reflecting means (4) within the housing and disposed in said path to divert the beam through an angle so as to emerge from the housing through an exit portion of the ultrasound transparent wall part, wherein the external dimension of the housing transverse to said path reduces substantially from the region of the transducer means to the region of the exit portion, characterised in that the reflecting means are mounted for rotation in the narrowed exit portion region.

2. A probe according to claim 1, the probe having a distal part, characterised in that the distal part of the probe has a smoothly contoured external shaping to permit safe non-invasive use.

3. A probe according to claim 1 or 2, characterised in that drive means to rotate the reflecting means is mounted within the housing.

4. A probe according to claim 3, characterised in that said drive means (8) is adapted to rotate the reflecting means in an oscillatory fashion.

5. A probe according to claim 1 characterised in that the reflecting means is mounted for rotation about an axis (7) lying along said beam path.

6. A probe according to claim 1 characterised in that the transducer means and the reflecting means are linked to rotate together.

7. A probe according to claim 1 characterised in that the reflecting means is mounted at an angle of about 45° to the direction of said beam path.

8. Apparatus for measuring parameters of fluid flow in a conduit within a human or animal body, comprising a probe according to claim 1 and signal processing means (22) to analyse Doppler components of the returning ultrasound signals.

9. A method for measuring parameters of fluid flow in a conduit within a human or animal body using the probe of any of claims 1 to 7, which method comprises:

locating the probe (1) to position the exit portion (14) adjacent the skin of the body;

operating the transducer means (2) to emit an ultrasound beam (3);

directing the ultrasound beam by way of the reflecting means (4) substantially along the conduit;

rotating the reflecting means so as to sweep the ultrasound beam through an arc;

detecting ultrasound beam signals returning from at least one range of the beam sweep and analysing the returning signals.

10. A method according to claim 9, characterised in that a parameter to be measured is the cross-section area of fluid flow in a conduit of substantially circular section.

11. A method according to claim 9 or 10 characterised in that the conduit is the ascending aorta (24) and the beam is directed by way of the suprasternal notch (26).

12. A method according to claim 10 characterised in that at least one velocity measurement is made and the cross-sectional area measured is multiplied by the velocity measurement to provide an estimate of fluid flow rate within the conduit.

* * * * *